United States Patent [19]
Pereira et al.

[11] Patent Number: 5,455,025
[45] Date of Patent: Oct. 3, 1995

[54] NON-AQUEOUS EMOLLIENT COMPOSITIONS FOR TOPICAL APPLICATION

[75] Inventors: Abel G. Pereira, Belleville; Kevin F. Gallagher, Middletown; Phillip G. Abend, Fort Lee; John C. Carson, Jr., Highland Park, all of N.J.

[73] Assignee: Croda, Inc., Parsippany, N.J.

[21] Appl. No.: 226,497

[22] Filed: Apr. 12, 1994

Related U.S. Application Data

[63] Continuation-in-part of Ser. No. 862,074, Apr. 2, 1992, Pat. No. 5,302,377.

[51] Int. Cl.$^6$ .............................. A61K 7/42; A61K 7/50; C07C 69/34; C07C 69/80
[52] U.S. Cl. .................. 424/59; 424/65; 424/66; 424/68; 424/70.1; 424/70.11; 514/785; 560/91; 560/94; 560/98; 560/182; 560/198; 560/204
[58] Field of Search ................... 424/59, 65, 66, 424/68, 70; 514/785; 560/91, 94, 98, 182, 198, 204

[56] References Cited

U.S. PATENT DOCUMENTS

| | | | |
|---|---|---|---|
| 3,746,744 | 7/1973 | Reid | 560/93 |
| 3,948,976 | 4/1976 | Suen et al. | 560/187 |
| 4,032,565 | 6/1977 | Kilpatrick et al. | 560/147 |
| 4,061,612 | 12/1977 | Bertozzi et al. | 524/290 |
| 4,359,478 | 11/1982 | Schmoller | 514/533 |
| 4,559,226 | 12/1985 | Fogel et al. | 424/66 |

FOREIGN PATENT DOCUMENTS 2834645  2/1980  Germany.

*Primary Examiner*—Arthur C. Prescott
*Attorney, Agent, or Firm*—Lerner, David, Littenberg, Krumholz & Mentlik

[57] ABSTRACT

Non-aqueous compositions for topical application comprising one or more active ingredients and a fatty alkoxylate ester emollient agent comprising a diester or triester of an aliphatic or aromatic tricarboxylic acid formed by reacting the acid with a stoichiometric excess of one or more polyalkoxylated fatty alcohols.

15 Claims, No Drawings

NON-AQUEOUS EMOLLIENT COMPOSITIONS FOR TOPICAL APPLICATION

CROSS-REFERENCE TO RELATED APPLICATION

The within application is a continuation-in-part of U.S. patent application Ser. No. 07/862,074 filed Apr. 2, 1992 which is now U.S. Pat. No. 5,302,377, issued Apr. 12, 1994, the disclosure of which is hereby incorporated herein by reference thereto.

BACKGROUND OF THE INVENTION

The present invention relates to fatty alkoxylate esters of aliphatic and aromatic dicarboxylic and tricarboxylic acids possessing unique emolliency properties. The fatty alkoxylate esters of the present invention are particularly useful in the formulation of cold creams, after shaves, anti-perspirants, lotions, skin moisturizers, electric pre-shaves, topical pharmaceutical ointments, lipsticks, hand and nail lotions and cleansing creams. The present invention further relates to topical preparations prepared from the fatty alkoxylate esters of the present invention.

Fatty acid esters of diols and polyols such as are disclosed in U.S. Pat. Nos. 4,803,010 to Ogino, 4,774,017 to Siebert, 4,614,622 to Huettinger and 4,097,403 to Tsutsumi are widely used as emulsifying thickeners. While these compounds function effectively as thickeners and emulsifiers, they lack emolliency.

German Patent No. 2,834,645 discloses fatty alcohol esters of citric acid, a tricarboxylic acid. The compounds are disclosed as being viscosity-stable cosmetic emulsifiers and thickeners; however, they lack the unique emolliency properties of the ester compositions described herein. Numerous other fatty citric acid esters are listed in the Cosmetic, Toiletry and Fragrance Association International Cosmetic Ingredient Directory, such as trioctyl citrate, trioctyldodecyl citrate, tristearyl citrate, triisostearyl citrate and trilauryl citrate. However, none of these citrates have the unique properties of the ester compositions described and claimed herein.

Mineral oil is widely used in personal care products as an emollient because of its low cost. However, mineral oil has an undesirable oily feel which is carried over into the finished product.

There exists a need for products that will reduce the oily feel of mineral oil without reducing its emolliency. Other than solid particle materials such as DRY-FLO® (aluminum starch octenylsuccinate) which is made by National Starch and Chemical of Bridgewater, N.J., there exists no other products which reduce the oily feel of mineral oil, petrolatum, and the like.

SUMMARY OF THE INVENTION

These needs are met by the present invention, which provides fatty alkoxylate esters of aliphatic and aromatic dicarboxylic and tricarboxylic acids which possess an exceptional dry emollient feel when compared to prior art emulsifying thickeners of similar molecular weight. It is therefore an object of the present invention to provide agents having improved emollient properties in the nature of two or more polyalkoxylated fatty alcohol chains covalently bonded by ester linkages to the carboxylic acid groups of aliphatic and aromatic dicarboxylic and tricarboxylic acids. Another object of the present invention is to provide a class of agents with superior emollient properties adaptable for use in formulating topical preparations and the like.

In accordance with one embodiment of the present invention, there is provided a fatty alkoxylate ester in which a diester or a triester of an aliphatic or aromatic dicarboxylic acid or tricarboxylic acid is formed by reacting the acid with a stoichiometric excess of one or more polyalkoxylated fatty alcohols. Preferred fatty alkoxylate esters of the present invention are citric acid esters having the structural formula of Formula I:

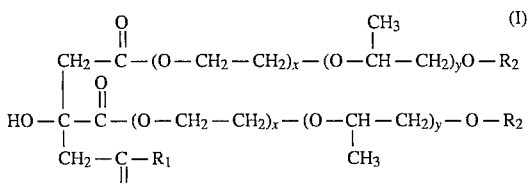

wherein $R_1$ is —OH or a polyalkoxylated fatty alcohol chain having the structural formula of Formula II:

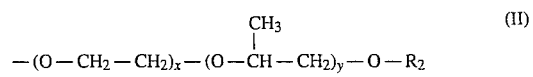

$R_2$ is a saturated or unsaturated, substituted or unsubstituted, aliphatic or aromatic fatty moiety containing from 8 to 22 carbon atoms; each x and y are independently zero or integers from 1 to 100, inclusive; the sum of x and y in each fatty alkoxy ester chain is independently between 1 and 200, inclusive; and the sum of all x's and y's does not exceed 600.

The present invention provides fatty alkoxylate esters possessing an exceptional aesthetic emollient feel that has long been desired by cosmetic chemists for use in personal care products. Therefore, in accordance with another embodiment of the present invention, there is provided an aqueous composition for topical application including one or more active ingredients, water and an emollient fatty alkoxylate ester of the present invention. Still yet another embodiment of the present invention provides a non-aqueous composition for topical application including one or more active ingredients and an emollient fatty alkoxylate ester of the present invention. The improved emollient feel of these esters enables cosmetic formulation chemists to produce products for topical application that out-perform similar products in aesthetic feel.

DETAILED DESCRIPTION OF THE PREFERRED EMBODIMENT

The emollient agents of the present invention are fatty alkoxylate esters of aliphatic or aromatic, dicarboxylic or tricarboxylic acids. Aliphatic dicarboxylic acids suitable for use in the present invention contain from 2 to 22 carbon atoms. Aliphatic tricarboxylic acids suitable for use in the present invention contain from 4 to 22 carbon atoms. Aromatic dicarboxylic acids suitable for use in the present invention contain from 8 to 22 carbon atoms, and aromatic tricarboxylic acids suitable for use in the present invention contain from 9 to 22 carbon atoms. Preferred aliphatic dicarboxylic acids contain from 3 to 8 carbon atoms. Preferred aliphatic tricarboxylic acids contain from 4 to 8 carbon atoms. Examples of suitable aliphatic dicarboxylic acids include malonic acid, succinic acid and maleic acid.

Preferred aromatic dicarboxylic acids contain from 8 to 12 carbon atoms. An example of a suitable aromatic dicarboxylic acid is phthalic acid. 1,2-phthalic acid, having the lowest melting point of the phthalic acid isomers, is preferred. Preferred aromatic tricarboxylic acids contain from 9 to 18 carbon atoms, and more preferably contain from 9 to 15 carbon atoms.

Tricarboxylic acids are preferred over dicarboxylic acids, and the dicarboxylic and tricarboxylic acids are preferably hydroxyl-substituted. Therefore, the most preferred aliphatic acid is the hydroxyl-substituted tricarboxylic acid, citric acid.

The fatty alkoxylate esters of the present invention are formed by reacting the above-described dicarboxylic and tricarboxylic acids with polyalkoxylated fatty alcohols. The polyalkoxylated fatty alcohols preferably have between about 1 and about 100 moles of the alkoxylating moieties present for each fatty alcohol moiety and are preferably either polyethoxylated, polypropoxylated or both polyethoxylated and polypropoxylated. Therefore, preferred polyalkoxylated fatty alcohols in accordance with the present invention have the structural formula of Formula III:

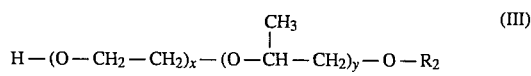

(III)

wherein $R_2$ is a saturated or unsaturated, substituted or unsubstituted aliphatic or aromatic fatty moiety containing from 8 to 22 carbon atoms. X and y are independently zero or integers from 1 to 100, inclusive, and the sum of x and y is between 1 and 100, inclusive.

The polyalkoxylated fatty alcohol depicted above is prepared by the polyalkoxylation of a saturated or unsaturated, substituted or unsubstituted, aliphatic or aromatic fatty alcohol having the structural formula of Formula IV:

(IV)

As is well understood by those of ordinary skill in the art, fatty alcohols are derived from fatty acids, and for this reason, groups such as $R_2$ are defined as fatty moieties. Fatty alcohols are often commercially prepared from a mixture of fatty acids and contain a mixture of fatty moieties. Therefore, in accordance with the present invention, $R_2$ for each polyalkoxylated fatty alcohol chain may be the same or different.

Saturated, unsubstituted, aliphatic fatty moieties containing from 8 to 18 carbon atoms are preferred, and such fatty moieties containing from 10 to 16 carbon atoms are even more preferred. The myristyl fatty moiety containing 14 carbon atoms is most preferred.

For diesters of dicarboxylic acids, aliphatic fatty moieties containing from 14 to 22 carbon atoms are suitable for use with the present invention. Diesters of dicarboxylic acids with ethoxylated 6-carbon alcohols are disclosed by U.S. Pat. No. 4,061,612 as being useful as plasticizers with extended temperature ranges in elastomers. This is attributable to the short 6-carbon alcohol chains, which provide a low molecular weight diester with low viscosity that consequently has the solvent properties required of a plasticizer.

The 14 to 22 carbon alcohols alkoxylated diesters of the present invention have high molecular weights and viscosities, and lack the solvent properties to function effectively as a plasticizer. Instead, the higher molecular weight and viscosity results in a diester having desireable emollient properties. Such emollient properties cannot be obtained from the lower molecular weight low viscosity diesters disclosed by U.S. Pat. No. 4,061,612.

Saturated, unsubstituted aliphatic moieties are preferred for the diesters of dicarboxylic acids of the present invention, and such fatty moieties containing from 14 to 18 carbon atoms are more preferred. Even more preferred are fatty moieties containing from 14 to 16 carbon atoms. The myristyl fatty moiety containing 14 carbon atoms is most preferred.

In the above-depicted polyalkoxylated fatty alcohol of Formula III, x and y are preferably independently selected from integers from 0 to 100, inclusive, and more preferably independently selected from integers from 0 to 10, inclusive. The sum of x and y is preferably between 1 and 200, inclusive, and more preferably between 1 and 20, inclusive.

As will be readily appreciated by those of ordinary skill in the art, the dicarboxylic acid-based esters of the present invention will be esterified on both carboxylic acid groups by the above-depicted polyalkoxylated fatty alcohol. The tricarboxylic acid-based compounds of the present invention will be esterified on either two or three carboxylic acid groups with the above-depicted polyakoxylated fatty alcohol. As described above, the sum of x and y in each polyalkoxylated fatty alcohol chain of Formula II is independently between 1 and 100, inclusive. However, the sum of all x's and y's in every polyalkoxylated fatty alcohol chain of Formula I should not exceed 600. The sum of all x's and y's preferably do not exceed 300, and more preferably do not exceed 60.

As noted above, preferred fatty alkoxylate esters in accordance with the present invention are di- and tri-fatty alkoxylate esters of citric acid having the structural formula of Formula I depicted above, wherein $R_1$ is —OH or a polyalkoxylated fatty alcohol chain having the structural formula of Formula II, wherein $R_2$, x and y are the same as described above with respect to Formula IV. The sum of each x and y in each polyalkoxylated fatty alcohol chain and the sum of all x's and y's in every polyalkoxylated fatty alcohol chain are the same as described above with respect to Formulas I and II.

With respect to Formulas I, II and III, when $R_2$ is a myristyl moiety, x is preferably zero and each y is preferably an integer independently selected from 1 to 100, inclusive, and more preferably an integer independently selected from 1 to 10. The sum of all y's preferably does not exceed 300, and more preferably does not exceed 30.

The fatty alkoxylate esters of the invention described above are prepared by initially reacting, either sequentially, or in their mixed forms, saturated or unsaturated, substituted or unsubstituted, aliphatic or aromatic fatty alcohols containing from 8 to 22 carbon atoms, with an epoxide, preferably ethylene oxide, propylene oxide, or mixtures thereof, in the presence of an acidic or basic catalyst. It is typical of propylene oxide to branch upon opening of the epoxide ring. This branching tends to impart liquidity to the compound. Catalysts suitable for this reaction are well-known in the art and include, for example, inorganic alkalis such as alkali metal oxides and hydroxides, e.g., potassium hydroxide, sodium methoxide, sodium borohydride, protic and Lewis acids, e.g., boron trifluoride, stannic chloride and sulfuric acid. Amines, quaternary ammonium compounds, water and other acids may also be employed. Mixtures of catalysts may also be employed. Certain reactive substrates known in the art, for example, acetylenic alkanols, may eliminate the need for such catalysts.

Preferably, a basic catalyst is used in this reaction and most preferably from about 0.1 to about 2.0 weight percent of potassium or sodium hydroxide, sodium methoxide, sodium borohydride or mixtures thereof, based on the weight of the alcohol. The reaction is carried out under anhydrous conditions to avoid formation of by-products, and at a temperature which is, preferably, in the range of from about 110° C. to about 200° C., although higher temperatures may be utilized. The reaction can be carried out at substantially atmospheric pressure, although it is preferably carried out in an autoclave at pressures of from about 10 psig to about 80 psig. The amount of ethylene oxide or propylene oxide introduced to the reaction zone, and the duration of reaction time, determines the number of moles of such components added to the fatty moiety, $R_2$, of the fatty alcohol.

In Formulas I, II and III, x represents the number of moles of ethylene oxide which are incorporated into each polyalkoxylate fatty alcohol chain. Likewise, y represents the number of moles of propylene oxide that are incorporated into the polyalkoxylated fatty alcohol chain. As will be readily appreciated by those of ordinary skill in the art, stoichiometric quantities of fatty alcohols, ethylene oxide and propylene oxide are reacted together, and stoichiometric quantities of the polyalkoxylated fatty alcohol and dicarboxylic acid or tricarboxylic acid are reacted together.

Preferably, the reaction is carried out sequentially in that the fatty alcohol is first reacted with the propylene oxide and after complete reaction, the ethylene oxide is introduced into the reaction. After complete reaction of the ethylene oxide, an acid, e.g., phosphoric acid or acetic acid, is introduced into the reaction mixture to neutralize the basic catalyst.

The resulting polyalkoxylated fatty alcohol is then reacted with a suitable dicarboxylic or tricarboxylic acid. Examples of suitable acids are listed above and include malonic acid, succinic acid, maleic acid, phthalic acid and citric acid. The most preferred acid is citric acid.

A conventional esterification reaction of the acid with the polyalkoxylated fatty alcohol is carried out. This may be accomplished with or without catalyst. Preferred catalysts are methane sulfonic acid and para-toluene sulfonic acid.

The esterification is typically performed by combining stoichiometric quantities of the polyalkoxylated fatty alcohol and the acid to be esterified. As is well understood by those of ordinary skill in the art, when two polyalkoxylated fatty alcohol chains are to be added to the acid, the polyalkoxylated fatty alcohol and acid to be esterified should be combined in a molar ratio of 2:1. When three polyalkoxylated fatty alcohol chains are to be added to the acid, the polyalkoxylated fatty alcohol and acid to be esterified should be combined in a molar ratio of 3:1. However, a slight stoichiometric excess should be employed to insure complete esterification and a low acidity. The polyalkoxylated fatty alcohol is a liquid, therefore a reaction solvent is not needed.

The polyalkoxylated fatty alcohol, acid and catalyst are combined with mixing to form a reaction mixture. The reaction mixture is heated with mixing at a temperature between about 155° C. and about 250° C., and preferably at a temperature between about 170° C. and 220° C. until, for the dicarboxylic acids and fully esterified tricarboxylic acids, an acid value of less than 8 mg KOH, and preferably less than 5 mg KOH is obtained. The reaction mixture is then cooled below 85° C. and washed with water, preferably without neutralizing the catalyst. Higher temperatures should be avoided to prevent loss of the polyalkoxylated fatty alcohols and, consequently, incomplete esterification and higher than desired acidity. The ester layer is separated and heated under vacuum until a moisture content of less than 0.2 percent is obtained.

As noted above, the polyalkoxylated fatty alcohols can be prepared by reacting mixed forms of fatty alcohols containing from 8 to 22 carbon atoms with mixtures of ethylene oxide and propylene oxide. Therefore, the resulting polyalkoxylated fatty alcohol can contain a mixture derived from the ethoxylation and the propoxylation of mixtures of fatty alcohols containing from 8 to 22 carbon atoms.

The fatty alkoxylate esters of the present invention are particularly useful as agents that confer superior emollient properties adaptable for use in a number of topical preparations. The esters are useful in the formulation of cold creams, after shaves, anti-perspirants, lotions, skin moisturizers, electric pre-shaves, topical pharmaceutical ointments, lipsticks, hand and nail lotions, cleansing creams, eye makeup formulations, cream rinses, sunscreens, cosmetic emulsions or gels in general, hairdressing preparations, foam baths and the like.

The emollient agent of the present invention is primarily useful as a replacement for the mineral oil and petrolatum emollient agents of the prior art. The emollient agent works well on its own or with reduced levels of mineral oil or petrolatum. A distinct improvement in emolliency properties of mineral oil or petrolatum-based products is noticeable when as little as 25% of the mineral oil or petrolatum has been replaced by the emollient agents of the present invention. Therefore, topical compositions in accordance with the present invention can include a second emollient agent of mineral oil, petrolatum, and the like present with the emollient of the present invention in a ratio of up to about 4:1 of the second emollient agent to the emollient agent of the present invention.

Aqueous topical preparations in accordance with the present invention include the essential compounds of the emollient agent of the present invention and one or more active ingredients, with the balance being water. As mentioned above, a second emollient agent of mineral oil, petrolatum and the like can optionally be included. Suitable active agents for use in topical preparations include sunscreens, moisturizers, film formers, detergents, thickening agents, emulsifiers, antiseptic agents, conditioning agents, deodorant actives, reducing agents for permanent wave products and the like. The detergent may include a variety of surfactants of the anionic type, non-ionic type, amphoteric type and mixtures thereof.

Suitable anionic detergents include sodium lauryl sulfate, sodium oleyl succinate, ammonium lauryl sulfosuccinate, sodium lauryl ether sulfate, ammonium lauryl sulfate, sodium dodecylbenzene sulfonate, triethanolamine dodecylbenzene sulfinate, sodium N-lauroyl sarcosinate, sodium laureth sulfate and triethanolamine lauryl sulfate. Suitable amphoteric or ampholytic detergents include N-lauryl-N'carboxymethyl-N-(2-hydroxyethyl) ethylenediamine, cocobetaine, the Miranol compounds in U.S. Pat. Nos. 2,528,378 and 2,781,354, cocoamidopropyl hydroxysultaine, lauroampho diacetate and cocoamidopropyl betaine. Other suitable amphoteric detergents include the quaternary cycloimidates, betaines and sultaines disclosed in U.S. Pat. No. 3,964,500. Nonionic surfactants include polysorbate 20, laurylamide DEA and sucrose monococate.

The topical preparations of the present invention, in addition to including the main components of the emollient agent of the present invention, one or more active ingredients, water and the optional second emollient agent, may also include coloring agents, fragrances, proteins, humectants, salts, preservatives, essential oils and the like. These additional components may be added in various amounts as is well-known in the cosmetic formulation art.

Typical aqueous topical preparations in accordance with the present invention include the emollient agents of the present invention, alone, or with the second emollient agent, in a range of from about 0.20 to about 40.0 percent by weight of the composition, preferably from about 3.0 to about 20.0 percent by weight of the composition. The one or more active ingredients may be present in an amount from about 0.20 to about 40.0 percent by weight of the composition, preferably from about 3.0 to about 20.0 percent by weight of the composition. As noted previously, the second emollient agent, when present, is blended with the emollient agent of the present invention in a ratio of up to about 4:1 of the second emollient agent to the emollient agent of the present invention.

Non-aqueous topical preparations in accordance with the present invention may also be prepared. Such preparations include the essential compounds of the emollient agent of the present invention and one or more of the above-listed active ingredients. A second emollient agent of mineral oil, petrolatum, and the like may again optionally be included, as may the above-described coloring agents, fragrances, proteins, humectants, salts, preservatives, essential oils and the like.

Typical non-aqueous topical preparations in accordance with the present invention include the emollient agents of the present invention, alone, or with the second emollient agent, in a range of from about 0.20 to about 99.0 percent by weight of the composition, preferably from about 10 to about 90.0 percent by weight of the composition, and more preferably from about 25 to about 75 percent by weight of the composition. The one or more active ingredients may be present in an amount from about 0.20 to about 99.0 percent by weight of the composition, preferably from about 10 to about 90.0 percent by weight of the composition, and more preferably from a bout 25 to about 75 percent by weight of the composition.

As with the aqueous topical preparations, the second emollient agent, when present, may be blended with the emollient agent of the present invention in a ratio of up to about 4:1 of the second emollient agent to the emollient agent of the present invention.

One non-aqueous composition in accordance with the present invention is a bath oil consisting entirely of from about 25 to about 99 percent by weight of the emollient agent of the present invention, from about 1 to about 75 percent by weight of mineral oil and optional coloring agents, fragrances, essential oils and the like. Preferred bath oils contain about 99 percent by weight of the emollient agent of the present invention.

A non-aqueous bath oil composition consisting entirely of the emollient agent of the present invention, with optional coloring agents, fragrances, essential oils and the like may also be prepared.

The topical preparations of the present invention are formulated utilizing techniques that are well-known in the cosmetic formulating art. Typically, the ingredients are combined with mixing and the addition of heat if necessary until a uniform, homogeneous product is formed. The water-soluble and water-insoluble ingredients are mixed together separately and combined with suitable emulsifying ingredients, such as the fatty alkoxylate esters of the present invention, to form emulsions.

The following non-limiting examples set forth hereinbelow illustrate certain aspects of the present invention. They are not to be considered limiting as to the scope and nature of the present invention.

EXAMPLES

EXAMPLE 1

Preparation of Tri-PPG-3 Myristyl Ether Citrate

Propylene oxide was bubbled into 685 g of myristyl alcohol in the presence of potassium hydroxide catalyst until three moles of propylene oxide were added per mole of myristyl alcohol, thus obtaining a pale, yellow liquid (PPG-3 myristyl ether) as the major product.

A four-necked flask was charged with 1,210 g of the PPG-3 myristyl ether and 190 g of citric acid. A catalytic amount of methane sulfonic acid was added to effect esterification, and the resulting reaction mixture was heated with stirring at 190° C. until an acid value of less than 8 mg KOH was obtained. The reaction mixture was cooled to 85° C. and washed with water. The ester layer was separated and heated under vacuum until a moisture content of less than 0.2 percent was obtained. Filter clay was added and the product was vacuum filtered, yielding tri-PPG-3 myristyl citrate, a clear, pale yellow liquid.

EXAMPLE 2

Preparation of DI-PPG-3 Myristyl Maleate

A four-necked flask was charged with 946 g of the PPG-3 myristyl ether of Example 1 and 54 g of maleic anhydride. A catalytic amount of methane sulfonic acid was added and the reaction mixture was heated at 120° C. until an acid value of less than 8 mg KOH was obtained. The product was cooled to 85° C. and washed with water. The ester layer was separated and heated under vacuum until a moisture content of less than 0.2 percent was obtained. Filter clay was added and the product was vacuum filtered, yielding di-PPG-3 myristyl maleate, a clear, pale yellow liquid.

The following examples, while not intended to be limiting, demonstrate topical preparations formulated in the nature of hand lotions and a hair conditioner in accordance with the present invention. All quantities listed are a percentage by weight unless otherwise indicated.

EXAMPLE 3

Preparation of Hand Lotion

A moisturizing hand lotion was prepared in accordance with the optimum formulation set forth below. Acceptable formula variations for the preparation of such hand lotions are also illustrated.

| Ingredient | Range | Preferred | Optimum |
|---|---|---|---|
| Part A | | | |
| Incroquat Behenyl TMS | 1.0–10.0 | 2.0–7.0 | 3.5 |
| Polawax | 1.0–10.0 | 2.0–7.0 | 3.0 |
| Stearyl Alcohol | 0–5.0 | 0.5–3.0 | 1.0 |
| Tri-PPG-3 Myristyl Citrate | 1.0–15.0 | 2.5–10.0 | 5.0 |
| Mineral Oil | 0–10.0 | 2.0–7.0 | 3.0 |
| Petrolatum | 0–10.0 | 2.0–7.0 | 4.0 |
| Part B | | | |
| Deionized Water | 5.0–9.0 | 60–85 | 74.5 |
| Glycerin | 1.0–15.0 | 2.5–10 | 5.0 |
| Part C | | | |
| Germaben II | 0.1–4.0 | 0.5–2.0 | 1.0 |

Incroquat Behenyl TMS, a behenyl trimonium methosulfate in cetearyl alcohol and Polawax, an emulsifying wax (NF), are available from Croda, Inc. Germaben II, a diazolidinyl urea, methyl paraben and propyl paraben-based preservative is available from Sutton Labs of Chatham, N.J.

The ingredients of Part A and Part B were separately mixed with heating to 75° C. The Part B mixture was then added to the Part A mixture with thorough mixing. The resulting mixture was cooled to 45° C. with continued mixing. The Part C ingredient was then added with mixing and the resulting mixture was cooled to room temperature with continued mixing.

The resulting hand lotion possessed typical skin moisturizing properties together with a surprisingly dry emollient feel.

EXAMPLE 4

Hand Lotion

A second moisturizing hand lotion was prepared in accordance with the optimum formulation set forth below. Acceptable formula variations are also illustrated.

| Ingredient | Range | Preferred | Optimum |
|---|---|---|---|
| Part A | | | |
| Di-PPG-3 Myristyl Maleate | 1.0–15.0 | 25–10.0 | 6.5 |
| Volpo 10 | 0.5–6.0 | 1.0–4.0 | 2.0 |
| Cetyl Alcohol | 0–10.0 | 1.0–6.0 | 3.0 |
| Lanolin Alcohol | 0–3.0 | 0.2–1.0 | 0.5 |
| Glyceryl Stearate | 0.5–6.0 | 1.0–4.0 | 2.0 |
| Mineral Oil | 0–10.0 | 2.0–6.0 | 4.0 |
| Part B | | | |
| Volpo S-20 | 0.1–5.0 | 0.5–2.0 | 0.75 |
| Incromectant AQ | 0.1–5.0 | 0.5–3.0 | 1.00 |
| Carbopol 934 | 0.01–1.0 | 0.1–0.5 | 0.20 |
| Glycerin | 0–10.0 | 1.0–6.0 | 3.00 |
| Deionized Water | 50.0–90.0 | 60.0–85.0 | 75.85 |
| Part C | | | |
| Germaben II | 0.1–4.0 | 0.5–2.0 | 1.00 |
| TEA 99% | 0.01–1.0 | 0.1–0.50 | 0.20 |

Volpo 10, an oleth-10, Volpo S-20, a steareth-20 and Incromectant AQ, an acetamidopropyl trimonium chloride, are all available from Croda, Inc. Carbopol 934, a carboxyvinyl polymer with active carboxyl groups, is available from B. F. Goodrich.

The Part A ingredients were combined and heated to 80° C. with mixing. The Part B ingredients were prepared by first dusting the Carbopol 934 in water and then stirring the mixture until completely dissolved. The remaining ingredients of Part B were added and heated to 80° C. with mixing. The Part B mixture was added to the Part A mixture with mixing. The resulting mixture was then cooled to 45° C. with continued mixing. The Part C ingredients were then added and the resulting mixture was allowed to cool to room temperature with continued mixing.

The resulting hand lotion possessed typical skin moisturizing properties together with a surprisingly dry emollient feel.

EXAMPLE 5

Hair Conditioner

A hair conditioner was prepared in accordance with the optimum formulation set forth below. Acceptable formula variations for the preparation of such hair conditioners are also illustrated.

| Ingredient | Range | Preferred | Optimum |
|---|---|---|---|
| Part A | | | |
| Stearalkonium Chloride | 0.5–5.0 | 1.0–2.5 | 1.25 |
| Polawax | 1.0–10.0 | 2.0–7.0 | 3.00 |
| Cetyl Alcohol | 0–7.5 | 0.5–5.0 | 2.00 |
| Crovol Pk-70 | 0–7.5 | 0.5–5.0 | 2.00 |
| Tri-PPG-3 Myristyl Citrate | 0.5–6.0 | 0.75–3.0 | 1.50 |
| Imcromectant AQ | 0.2–4.0 | 0.5–2.5 | 1.00 |
| Deionized Water | 60.0–95.5 | 75.0–90.0 | 88.25 |
| Part B | | | |
| Germaben II | 0.1–4.0 | 0.5–2.0 | 1.00 |

Crovol Pk-70, a PEG-45 palm kernel glyceride, is available from Croda, Inc.

The resulting product possessed characteristic hair conditioning properties together with a desirable dry emollient feel.

EXAMPLE 6

Comparative Example

Trimyristyl Citrate was prepared by esterifying non-propoxylated myristyl alcohol with citric acid under the same conditions as described in Example I, but for the propoxylation step. The product was a white solid with a melting point of 38° C. The product also had very poor emolliency properties on its own, was marginally compatible with mineral oil at room temperature, and did not exhibit the reduction in oily feel of mineral oil as seen with the alkoxylated alcohol citrate esters. The improved emolliency of the compounds of the present invention would appear to be attributable, in part, to the alkoxylation of the fatty alcohols prior to esterification.

The foregoing description of the preferred embodiment should be taken as illustrating, rather than as limiting the present invention as defined by the claims. Numerous variations and combinations of the features described above can be utilized without departing from the present invention.

What is claimed is:

1. A non-aqueous composition for topical application comprising one or more active ingredients and a fatty alkoxylate ester emollient agent comprising a diester or triester of an aliphatic or aromatic tricarboxylic acid formed by reacting said acid with a stoichiometric excess of one or more polyalkoxylated fatty alcohols.

2. The composition of claim 1, wherein said one or more active ingredients are selected from the group consisting of sunscreens, moisturizers, film formers, detergents, emulsifiers, thickening agents, antiseptic agents, conditioning agents, deodorant actives and reducing agents for permanent wave products.

3. The composition of claim 2, wherein said active ingredients comprise a detergent selected from the group consisting of anionic surfactants, non-ionic surfactants, amphoteric surfactants and mixtures thereof.

4. The composition of claim 1, wherein said one or more active ingredients are present in an amount in the range of about 25 to about 75 percent by weight of said composition.

5. The composition of claim 1, wherein said emollient agent is present in an amount in the range of about 25 to about 75 percent by weight of said composition.

6. The composition of claim 1, wherein said fatty alkoxylate ester comprises a diester or a triester of an aliphatic tricarboxylic acid containing from 4 to 22 carbon atoms.

7. The composition of claim 1, wherein said aliphatic or aromatic tricarboxylic acid is hydroxyl-substituted.

8. The composition of claim 7, wherein said hydroxyl-substituted acid is citric acid.

9. The composition of claim 1, wherein said polyalkoxylated fatty alcohol is selected from the group consisting of polyethoxylated fatty alcohols, polypropoxylated fatty alcohols and fatty alcohols that are both polyethoxylated and polypropoxylated.

10. The composition of claim 1, wherein said fatty alkoxylate ester comprises a fatty alkoxylate ester having the structural formula:

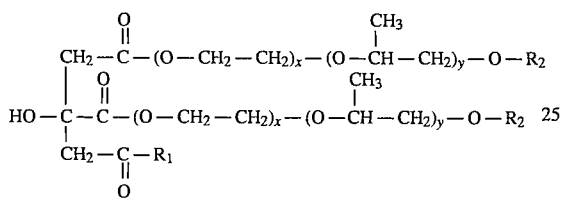

wherein $R_1$ is —OH or a polyalkoxylated fatty alcohol chain having a structural formula:

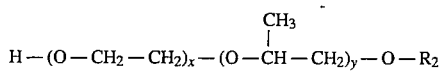

wherein $R_2$ is a saturated or unsaturated, substituted or unsubstituted, aliphatic or aromatic fatty moiety containing from 8 to 22 carbon atoms; each x and y are independently selected from the group consisting of zero and integers from zero to 100, inclusive; the sum of x and y of each polyalkoxylated fatty alcohol chain is independently between 1 and 200, inclusive; and the sum of all x's and y's in all of said polyalkoxylated fatty alcohol chains is less than 600.

11. The composition of claim 10, wherein $R_1$ is a polyalkoxylated fatty alcohol chain having the structural formula:

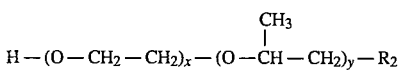

12. The composition of claim 10, wherein $R_2$ comprises a saturated, unsubstituted aliphatic fatty moiety containing from 8 to 18 carbon atoms.

13. The composition of claim 12, wherein $R_2$ comprises a myristyl fatty moiety, x is zero, each y is independently between 1 and 100, inclusive, and the sum of all y's does not exceed 300.

14. The position of claim 1, further comprising a second emollient agent selected from the group consisting of mineral oil, petrolatum and mixtures thereof, wherein said second emollient agent is present at up to about a 4:1 ratio with respect to said fatty alkoxylate ester emollient agent.

15. A bath oil composition consisting essentially of:
(a) a fatty alkoxylate ester emollient agent consisting of a diester or triester of an aromatic or aliphatic tricarboxylic acid formed by reacting said acid with a stoichiometric excess of one or more polyalkoxylated fatty alcohols; and
(b) Up to about 75% by weight of mineral oil.

* * * * *